(12) United States Patent
Balwani

(10) Patent No.: US 10,425,304 B2
(45) Date of Patent: Sep. 24, 2019

(54) METHODS AND SYSTEMS FOR NETWORK CONNECTIVITY

(71) Applicant: Theranos, Inc., Palo Alto, CA (US)

(72) Inventor: Sunny Balwani, Palo Alto, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 14/511,861

(22) Filed: Oct. 10, 2014

(65) Prior Publication Data
US 2015/0106514 A1    Apr. 16, 2015

Related U.S. Application Data

(63) Continuation of application No. 13/764,642, filed on Feb. 11, 2013, now Pat. No. 8,862,750, which is a continuation of application No. 13/244,836, filed on Sep. 26, 2011, now Pat. No. 8,392,585.

(51) Int. Cl.
| | |
|---|---|
| *H04L 12/24* | (2006.01) |
| *G16H 10/20* | (2018.01) |
| *H04L 12/26* | (2006.01) |
| *H04W 76/18* | (2018.01) |
| *H04L 12/707* | (2013.01) |

(Continued)

(52) U.S. Cl.
CPC ......... *H04L 43/0811* (2013.01); *G16H 10/20* (2018.01); *H04L 41/0654* (2013.01); *H04L 43/10* (2013.01); *H04L 45/22* (2013.01); *H04L 45/28* (2013.01); *H04L 47/728* (2013.01); *H04L 47/746* (2013.01); *H04W 76/18* (2018.02)

(58) Field of Classification Search
CPC ............... H04L 43/0811; H04L 45/00; H04L 29/08234; H04L 41/0654; H04L 43/10; H04L 45/22; H04L 45/28; H04L 47/728; H04L 47/746; H04L 67/1023; G06F 13/00; G06F 19/363; H04W 76/027
USPC .................. 709/217, 219, 227, 228, 250
See application file for complete search history.

(56) References Cited

U.S. PATENT DOCUMENTS

| | | |
|---|---|---|
| 6,115,545 A | 9/2000 | Mellquist |
| 6,148,198 A | 11/2000 | Anderson et al. |

(Continued)

FOREIGN PATENT DOCUMENTS

| | | |
|---|---|---|
| EP | 1995918 A1 | 11/2008 |
| WO | 2000074313 A1 | 12/2000 |

(Continued)

OTHER PUBLICATIONS

International search report and written opinion dated Nov. 5, 2012 for PCT/US2012/057093.

(Continued)

*Primary Examiner* — Viet D Vu

(57) ABSTRACT

Methods and systems are provided for connecting an electronic device to a network. In some situations, the electronic device connects to a first network provider and pings a first server having a static internet protocol address and a second server having a dedicated uniform resource locator. If the electronic device receives a response from the first and second server, the electronic device maintains its connection to the first network provider. Otherwise, the electronic device connects to a second network provider and pings the first and second servers.

20 Claims, 6 Drawing Sheets

(51) Int. Cl.
*H04L 12/911* (2013.01)
*H04L 12/703* (2013.01)

(56) References Cited

U.S. PATENT DOCUMENTS

| | | | |
|---|---|---|---|
| 6,173,411 B1 * | 1/2001 | Hirst | H04L 12/2697 709/223 |
| 6,760,775 B1 | 7/2004 | Anerousis et al. | |
| 6,859,830 B1 | 2/2005 | Ronneburg et al. | |
| 7,359,339 B2 | 4/2008 | Benson et al. | |
| 7,472,192 B2 | 12/2008 | DeFerranti et al. | |
| 7,587,201 B2 | 9/2009 | Ohara | |
| 7,609,654 B2 | 10/2009 | Lubeck et al. | |
| 7,650,395 B2 | 1/2010 | Johnson et al. | |
| 7,711,800 B2 | 5/2010 | Gavrilescu et al. | |
| 7,978,665 B1 | 7/2011 | Jaynes et al. | |
| 8,287,820 B2 | 10/2012 | Williams et al. | |
| 8,392,585 B1 | 3/2013 | Balwani | |
| 8,588,807 B2 | 11/2013 | Kumar | |
| 8,862,750 B2 | 10/2014 | Balwani | |
| 2001/0056503 A1 * | 12/2001 | Hibbard | G06F 11/2012 709/250 |
| 2002/0144187 A1 * | 10/2002 | Morgan | G06F 11/0748 714/43 |
| 2004/0093619 A1 * | 5/2004 | Cox | H04N 5/445 725/110 |
| 2004/0127252 A1 | 7/2004 | Tsunomoto et al. | |
| 2004/0198360 A1 | 10/2004 | Kotzin | |
| 2005/0068972 A1 | 3/2005 | Burns et al. | |
| 2005/0254435 A1 | 11/2005 | Moakley et al. | |
| 2006/0084417 A1 | 4/2006 | Melpignano et al. | |
| 2007/0255733 A1 | 11/2007 | Chahal et al. | |
| 2008/0002716 A1 | 1/2008 | Wiley et al. | |
| 2009/0013210 A1 * | 1/2009 | McIntosh | H04L 12/2697 714/4.1 |
| 2009/0094361 A1 | 4/2009 | Srinivasan | |
| 2009/0124284 A1 | 5/2009 | Scherzer et al. | |
| 2010/0082781 A1 | 4/2010 | Lubeck et al. | |
| 2010/0246416 A1 | 9/2010 | Sinha et al. | |
| 2011/0116385 A1 | 5/2011 | Turlington et al. | |
| 2013/0122910 A1 | 5/2013 | Singh et al. | |
| 2013/0262666 A1 | 10/2013 | Balwani | |
| 2016/0127152 A1 | 5/2016 | Balwani | |
| 2017/0317903 A1 | 11/2017 | Balwani | |

FOREIGN PATENT DOCUMENTS

| | | |
|---|---|---|
| WO | 2007099414 A1 | 9/2007 |
| WO | 2010112059 A1 | 10/2010 |
| WO | 2014138137 A2 | 9/2014 |

OTHER PUBLICATIONS

Office Action dated Feb. 20, 2014 for U.S. Appl. No. 13/764,642.
Office Action dated Mar. 26, 2012 for U.S. Appl. No. 13/244,836.
Office Action dated Jul. 13, 2012 for U.S. Appl. No. 13/244,836.
Office Action dated Sep. 16, 2013 for U.S. Appl. No. 13/764,642.
International Search Report and Written Opinion dated Sep. 4, 2014 for PCT/US2014/020440.
Office Action dated Apr. 14, 2015 for U.S. Appl. No. 13/784,814.
Office Action dated Nov. 10, 2015 for U.S. Appl. No. 13/784,814.
Office Action dated Mar. 14, 2016 for U.S. Appl. No. 14/842,678.
Office Action dated May 25, 2016 for U.S. Appl. No. 13/784,814.
Notice of Allowance dated Dec. 9, 2016 for U.S. Appl. No. 13/784,814.
Office Action dated Mar. 22, 2018 for U.S. Appl. No. 15/429,551.

* cited by examiner

METHODS AND SYSTEMS FOR NETWORK CONNECTIVITY

CROSS REFERENCE

This Application is a continuation application of patent application Ser. No. 13/244,836, filed on Sep. 26, 2011 now issued as U.S. Pat. No. 8,392,585, which is incorporated herein by reference in its entirety and to which application we claim priority under 35 USC § 120.

A Computer network is a collection of computers and devices interconnected by communications channels that facilitate communications. A computer network may allow sharing of resources and information among interconnected devices. A network may include the Internet, an intranet, and the extranet.

A local area network (LAN) is typically a small network constrained to a small geographic area. A metropolitan area network (MAN) is typically a network constrained to metropolitan area, such as a city. A wide area network (WAN) is typically a network that covers a large geographic area. Wireless LANs are typically the wireless equivalents of LANs and WANs.

Networks may be interconnected to allow communication with a variety of different kinds of media, including twisted-pair copper wire cable, coaxial cable, optical fiber, power lines and various wireless technologies. A network may include routers and routing protocols.

SUMMARY OF THE INVENTION

In an aspect of the invention, computer-implemented methods for testing network connectivity for a network device comprise connecting to a network provider; pinging a first server having a static internet protocol (IP) address with the aid of the network provider; pinging a second server having a static uniform resource locator (URL) with the aid of the network provider; and determining whether to maintain connectivity to said network provider based on whether a response was received by said network device from said first server and/or whether a response was received by said network device from said second server. In an embodiment, determining whether to maintain connectivity to said network provider is based on whether a response was received by said network device from said first server and whether a response was received by said network device from said second server.

In some situations, said computer-implemented methods further comprise connecting to an another network provider based on at least one criterion selected from the group consisting of a bandwidth of the another network provider, cost to maintain connectivity to the another network provider, cost to transmit information with the aid of the another network provider, a download rate of the another network provider and an upload rate of the another network provider. In an embodiment, the at least one criterion is location-based, time based or bandwidth-based.

In an embodiment, pinging said first server comprises sending a ping packet to the first server. In another embodiment, pinging said second server comprises sending a ping packet to the second server. In another embodiment, connectivity to the network provider is maintained if the first server responds to the network device in response to said pinging the first server and/or the second server responds to the network device in response to said pinging the second server. In another embodiment, said computer-implemented methods further comprise connecting to another network provider if the first server does not respond to the network device in response to said pinging the first server and/or the second server does not respond to the network device in response to said pinging the second server. In another embodiment, the network provider is selected from the group consisting of a wireless router, Bluetooth router, wired router, cellular network router, radiofrequency (RF) device and optoelectronic device.

In some situations, said computer-implemented methods further comprise connecting to an additional network provider; pinging the first server with the aid of the additional network provider; pinging the second server with the aid of the additional network provider; and determining whether to maintain connectivity to the additional network provider based on whether a response was received by the network device from the first server and/or whether a response was received by the network device from the second server. In an embodiment, determining whether to maintain connectivity to the additional network provider is based on whether a response was received by the network device from the first server and whether a response was received by the network device from the second server. In another embodiment, connecting to said second network provider comprises terminating connectivity to said network provider.

In an embodiment, said network provider is selected from the group consisting of a wireless router, Bluetooth router, wired router, cellular network router, radiofrequency (RF) device and optoelectronic device. In another embodiment, the first and second servers are pinged simultaneously.

In some embodiments, computer-implemented methods for testing network connectivity for a network device comprise connecting to a network provider; directing a first data packet from the network device to a first server having a static internet protocol (IP) address, wherein the first data packet is directed with the aid of the network provider; directing a second data packet from the network device to a second server having a static uniform resource locator (URL), wherein the second data packet is directed with the aid of the network provider; and determining whether to maintain connectivity to the network provider based upon a comparison of one or more data packets received by the network device from the first server and the second server. In an embodiment, the first server comprises a domain name system (DNS) server. In another embodiment, the first data packet is an echo request packet. In another embodiment, the second data packet is an echo request packet. In another embodiment, directing said first data packet from said network device to said first server comprises pinging the first server. In another embodiment, directing said second data packet from said network device to said second server comprises pinging the second server. In another embodiment, connectivity to the network provider is maintained if a first received data packet of said one or more data packets received by the network device is the same as the first data packet directed to the first server. In another embodiment, connectivity to the network provider is maintained if a second received data packet of said one or more data packets received by the network device is the same as the second data packet directed to the second server.

In some situations, the computer-implemented methods further comprise receiving a first received data packet from the first server and/or receiving a second received data packet from the second server. In an embodiment, connectivity to the network provider is maintained if a checksum of the first received data packet matches a predetermined data packet. In another embodiment, connectivity to the network provider is maintained if a checksum of the second received data packet matches a predetermined data packet. In an embodiment, the computer-implemented methods further comprise connecting to another network provider if the first received data packet is different from the first data packet and/or the second received data packet is different from the second data packet.

In some situations, the computer-implemented methods further comprise connecting to an another network provider; directing the first data packet from the network device to the first server, wherein the first data packet is directed with the aid of the another network provider; directing the second data packet from the network device to the second server, wherein the second data packet is directed with the aid of the another network provider; and determining whether to maintain connectivity to the other network provider based upon a comparison of one or more data packets received by the network device from the first server and the second server. In an embodiment, connecting to said another network provider comprises terminating connectivity to said network provider.

In an embodiment, connecting to said network provider comprises locating said network provider. In an embodiment, said network provider is selected from the group consisting of a wireless router, Bluetooth router, wired router, cellular network router, radiofrequency (RF) device and optoelectronic device.

In an embodiment, said computer-implemented methods further comprise determining whether to maintain connectivity to the network provider based on at least one criterion selected from the group consisting of bandwidth, cost to maintain connectivity to the network provider, cost to transmit information with the aid of the network provider, the download rate and the upload rate. In an embodiment, the at least one criterion is location-based, time based or bandwidth-based.

In some situations, said computer-implemented methods further comprise connecting to another network provider based on at least one criterion selected from the group consisting of the bandwidth of the other network provider, cost to maintain connectivity to the other network provider, cost to transmit information with the aid of the other network provider, the download rate of the other network provider and the upload rate of the other network provider. In an embodiment, connectivity to the network provider is maintained upon comparison of a download rate or an upload rate to a predetermined limit. In an embodiment, the network device is selected from the group consisting a personal computer (PC), tablet PC, slate PC, server, mainframe and Smart phone.

In some embodiments, computer-implemented methods for selecting a network provider for a network device comprise connecting to the network provider; pinging, with the aid of the network provider, a first server having a static internet protocol (IP) address and a second server having a static uniform resource locator (URL); and terminating a connection to said network provider based upon any one network termination condition selected from the group consisting of (a) a response was not received by the network device from said first server and/or said second server after said pinging, (b) a network bandwidth (or latency, performance or cost-related factors) of another network provider is higher than a network bandwidth of said network provider, (c) a network cost of another network provider is lower than a network cost of said network provider, (d) network access provided by another network provider is more robust than network access provided by said network provider, (e) connectivity between the network device and another network provider is via wired connection and connectivity between the network device and said network provider is via wireless connection and (f) another network provider is in closer proximity to the network device than said network provider. In an embodiment, the connection to said network provider is terminated based upon at least any two network termination conditions selected from said group. In another embodiment, the connection to said network provider is terminated based upon at least any three network termination conditions selected from said group. In another embodiment, the computer-implemented method further comprises connecting to an another network provider. In another embodiment, connectivity between the network device and the first network provider is via a wired or wireless network access point. In another embodiment, the first and second servers are pinged simultaneously.

In some embodiments, computer-implemented methods for establishing network connectivity for a network device comprise the steps of (a) connecting to a first network provider; (b) pinging, with the aid of the first network provider, a first server and a second server; and (c) selecting a second network provider over said first network provider if said second network provider meets a criterion unmet by said first network provider. In an embodiment, said selecting is in response to said pinging. In another embodiment, said criterion is a location-based, time based or bandwidth-based criterion. In another embodiment, said first server has a static internet protocol (IP) address. In another embodiment, said second server has a static uniform resource locator (URL). In another embodiment, said criterion is selected from the group consisting of (a) whether a response was received by the network device from said first server and/or said second server after said pinging, (b) whether a network bandwidth of said second network provider is higher than a network bandwidth of said first network provider, (c) whether a network cost of said second network provider is lower than a network cost of said first network provider, (d) whether network access provided by said second network provider is more robust than network access provided by said first network provider, (e) whether connectivity between said network device and said second network provider is via wired connection and connectivity between said network device and said first network provider is via wireless connection, and (f) whether said second network provider is in closer proximity to the network device than said first network provider.

In some embodiments, computer-implemented method for establishing network connectivity for a network device comprise connecting to a first network provider; locating a second network provider, the second network provider having a higher ranked order of preference than the first network provider based on one or more predetermined network connectivity criteria; and connecting to the second network provider. In an embodiment, said locating comprises pinging a first server and a second server. In another embodiment, said first server has a static internet protocol (IP) address. In another embodiment, said second server has a static uniform resource locator (URL). In another embodiment, said one or more predetermined network connectivity criteria are selected from the group consisting of network bandwidth, network cost and proximity of the network device to a network provider. In another embodiment, said one or more predetermined network connectivity criteria are location-based, time based or bandwidth-based.

In some embodiments, one or more steps of the methods provided herein are performed with the aid of a processor. In an example, the network device is connected to the first network provider with the aid of a processor. In some embodiments, any of pinging, selecting and locating are performed with the aid of one or more processors, which may be located in network devices provided herein or remotely, such as in remote computer systems.

In another aspect of the invention, systems for establishing network connectivity for a network device comprise a network connectivity controller for locating network providers, the network connectivity controller having a processor for executing machine-readable code configured to: establish a connection to a network provider; ping a first server having a static internet protocol (IP) address with the aid of the network provider; ping a second server having a static uniform resource locator (URL) with the aid of the network provider; and determine whether to maintain connectivity to said network provider based on whether a response was received by said network device from said first server and/or whether a response was received by said network device from said second server. The system further comprises a graphical user interface (GUI) for displaying a list of network providers to a user, the list of network providers generated with the aid of one or more network connectivity criteria. In an embodiment, said one or more network connectivity criteria are selected from the group consisting of a bandwidth of another network provider, cost to maintain connectivity to another network provider, cost to transmit information with the aid of another network provider, a download rate of another network provider and an upload rate of another network provider. In another embodiment, said one or more network-connectivity criteria are location-based, time based or bandwidth-based. In another embodiment, said machine-readable code is configured to determine whether to maintain connectivity to said network provider based on whether a response was received by said network device from said first server and whether a response was received by said network device from said second server.

In another aspect of the invention, computer-readable mediums comprise code implementing methods, the methods comprising establishing a connection to a network provider; pinging a first server having a static internet protocol (IP) address with the aid of the network provider; pinging a second server having a static uniform resource locator (URL) with the aid of the network provider; and determining whether to maintain connectivity to said network provider based on whether a response was received by said network device from said first server and/or whether a response was received by said network device from said second server. In some cases, the connection to the network provider is established with the aid of a processor.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
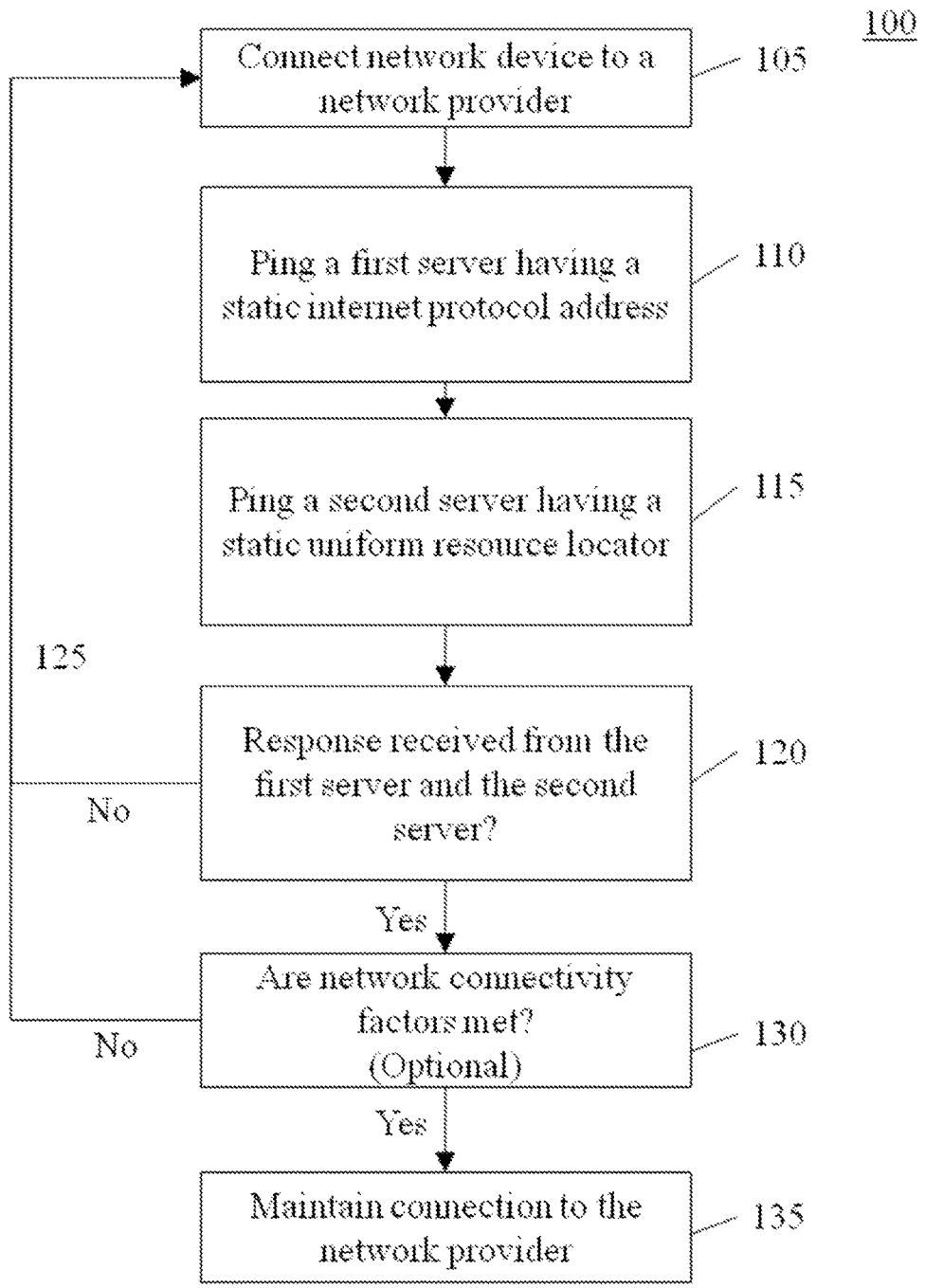
FIG. 1 shows a method for connecting a network-enabled device (also "network device" herein) to a network, in accordance with an embodiment of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "network," as used herein, refers to a local area network (LAN), metropolitan area network (MAN), or wide area network (WAN). In some situations, a network includes the Internet. A network includes wired and/or wireless components.

The term "router," as used herein, refers to a device that forwards or relays data packets across one or more networks.

The term "network provider," as used herein, refers to one or more computer systems or devices for providing network connectivity to, or facilitating network connectivity for, an electronic device. In some situations, a network provider is a router or a plurality of routers.

The term "electronic device," as used herein, refers to a computer device configured to connect to a network. In some cases, an electronic device is a portable electronic device. Examples of electronic devices include Smart phones (e.g., iPhone®, Android®-enabled phone, HTC® phone, Blackberry®), laptops, tablet personal computers (e.g., iPad®), and desktop computers (e.g., workstations, servers), cameras, gaming stations (e.g., Sony® PlayStation®, Microsoft® Xbox), televisions, music players (e.g., MP3 players, radios, CD players) and video players (e.g., DVD players). Electronic devices may be included in other components. For instance, an electronic device may be part of a residential or commercial building, vehicle, or aircraft.

The term "network-enabled device," as used herein, refers to an electronic device configured to connect to, reconnect to, and communicate with one or more electronic devices with the aid of a network. In some example, a network-enabled device (also "network device" herein) includes a Smart phone and personal computer (PC). As an example, a network-enabled device is a desktop personal computer (PC), laptop PC, mainframe computer, set-top box, personal digital assistant, cellular telephone, media player, web pad, tablet PC, slate PC, or Smart phone. In some situations, a network-enabled device includes a network interface for facilitating network connectivity. A network interface includes, for example, an Ethernet interface for connectivity to a network through a wired connection, or a wireless interface for connectivity to a wireless provider that in turn provides connectivity to a network. A network-enabled device may include multiple wireless interfaces. A wireless provider may include one or more of a Wi-Fi (or WiFi) router and one or more channel access methods. In some cases, a channel access method is selected from frequency division multiple access (FDMA), wavelength division multiple access (WDMA), orthogonal frequency division multiple access (OFDMA), based on Orthogonal, frequency-division multiplexing (OFDM), single-carrier FDMA (SC-FDMA) (or linearly-precoded OFDMA (LP-OFDMA)), time-division multiple access (TDMA), code division multiple access (CDMA) (or spread spectrum multiple access (SSMA)), direct-sequence CDMA (DS-CDMA), frequency-hopping CDMA (FH-CDMA), orthogonal frequency-hopping multiple access (OFHMA), multi-carrier code division multiple access (MC-CDMA), space division multiple access (SDMA), packet mode channel access methods (e.g., contention based random multiple access methods), duplexing methods (e.g., time division duplex (TDD), frequency division duplex (FDD)), global system for mobile communications (GSM), GSM with GPRS packet, bluetooth packet mode communication, IEEE 802.11b wireless local area networks (WLAN's), high performance radio local area network (HIPERLAN/2) wireless networks, and G.hn. A wireless provider may be configured for second-generation wireless telephone technology (2G), third generation mobile telecommunications (3G), fourth generation cellular wireless standards (4G) or LTE Advanced (LTE) communication standard.

A network-enabled device may include multiple interfaces. In some cases, a network-enabled device includes an Ethernet interface and wireless interfaces for connectivity to a WiFi router, CDMA provider and/or GSM provider.

The term "static," as used in the context of network parameters herein, refers to a network parameter that does not change during a finite period of time, such as a set or predetermined period of time. A static internet protocol (IP) address is an address that does not change within a predetermined (or set) period of time. In some situations, a static IP address is a dedicated IP address. A static uniform resource locator (URL) is a network (or web) address that does not change within a predetermined period of time. In some situations, a static URL is a dedicated URL, such as a URL dedicated to an entity (e.g., business, individual). A static URL may be associated with one or more servers of the entity.

The term "connectivity," as used herein, refers to a network-enabled electronic device being in network communication with a network provider, such as a router (e.g., wired router, wireless router). A network-enabled device has connectivity to a network provider if the network-enabled device is able to communicate with the network provider, such as ping the network provider or send data (e.g., data packets) to or receive data from the network provider.

The term "ping," as used herein, refers to a computer network administration utility used to test the reachability of a host on a network (including, but not limited to, an Internet Protocol (IP) network) and to measure the round-trip time for messages sent from the originating host to a destination computer. In some situations, during pinging, one or more bits of information are sent from a network device to a server through a network provider. In some cases, pinging is also a utility that sends (or transmits) internet control message protocol (ICMP) messages to test for connectivity. In some cases, pinging employs a low-level protocol, such as Internet Protocol (IP) or Transmission Control Protocol (TCP), or other protocols, such as Hypertext Transfer Protocol (HTTP), SSH, or Simple Mail Transfer Protocol (SMTP). In some situations, a ping packet includes a data packet that enables a user to check or investigate various network connectivity factors, such as connectivity, speed, bandwidth and/or response time.

There are methods currently available for connecting an electronic device, such as a portable electronic device, to a network. However, as recognized herein, such methods have limitations. For example, in certain cases methods for connecting a portable electronic device to a network do not establish the most optimum connection, which may be assessed on the basis of network cost, network bandwidth and proximity to a router, for example. As another example, current methods for establishing network connectivity may not continually optimize network connectivity in view of changing conditions, such as proximity to a router and network bandwidth. Recognized herein is the need for improved methods for connecting an electronic device to a network.

Methods provided herein enable a network-enabled electronic device to connect and reconnect to a network and, in some cases, optimize or improve its network connectivity. In certain cases, methods provided herein enable a network-enabled electronic device to connect to a network that is optimum in view of one or more connectivity criteria (or rules) provided herein. In other cases, if an optimum connectivity is not established, methods provided herein enable a network-enabled electronic device to continually optimize network connectivity in view of changing conditions.

Network Connectivity Methods

In an aspect of the invention, a method for establishing network connectivity for a network-enabled device comprises the network-enabled electronic device (also "network-enabled device" herein) connecting to a network provider. Next, the network-enabled device pings a first server having a static internet protocol (IP) address with the aid of the network provider. The network-enabled device also pings a second server having a static uniform resource locator (URL) with the aid of the network provider. The first and second servers may be pinged simultaneously or sequentially (i.e., the first after the second or the second after the first). Next, the network-enabled device determines whether to maintain connectivity to the network provider based on whether the network-enabled device receives a response from the first server and/or whether the network-enabled device receives a response from the second server. The response in each case may be a confirmation that the first and second servers were pinged by the network-enabled device.

In some cases, upon pinging the second server having the static (or dedicated) URL (e.g., "Google.com"), a domain name system (DNS) server in communication with the network provider resolves the URL to an IP address of the second server. A ping packet is then sent to the second server (at the resolved IP address). A response is generated by the second server and sent to the network provider and subsequently to the network-enabled device. The lack of a response from the second server may indicate that the second server is malfunctioning (or unavailable or unreachable) or that the DNS server in communication with the network provider is malfunctioning. In such a case, the network-enabled device may ping a third server having a dedicated URL (e.g., "Yahoo.com"). The DNS server in communication with the network provider resolves the URL to an IP address of the third server. A ping packet is then sent to the third server (at the resolved IP address). If a response is not received by the network-enabled device from the third server, then the network-enabled device may concluded that the DNS server in communication with the network provider is malfunctioning. In such a case, the network-enabled device connects to another network provider and the steps above are repeated.

In some situations, the network provider is selected from the group consisting of a wireless router, Bluetooth router, wired router, cellular network router, radiofrequency (RF) device and optoelectronic device. The first server has a static IP address (e.g., "123.123.123.123") and the second server has a static URL (e.g., "Google.com"). In some cases, the static URL is updated, such as upon a network update.

In some cases, the first server is identified by a user-determined IP address, i.e., an IP address that is determined or provided by a user operating the network-enabled device. In such a case, the user may input the IP address of the first server into a network configuration utility of the network-enabled device, for example. Similarly, in some cases the second server is designated by a URL that is user-determined. For example, in the network configuration utility the user provides a string that defines the URL of the second server.

In an embodiment, the first server and second server are pinged simultaneously. In another embodiment, the first server is pinged before the second server. In another embodiment, the second server is pinged before the first server. Pinging the first and second servers involves sending (or directing) a ping packet from the network-enabled device to each of the first and second servers. In another embodiment, only the first or second server is pinged. In such a case, the response after pinging the first or second server is assessed to determine whether to maintain connectivity to the network provider.

In some embodiments, additional servers are pinged. In an embodiment, a third server having a static IP address or dedicated (or static) URL is pined. In another embodiment, at least 2, or 3, or 4, or 5, or 6, or 7, or 8, or 9, or 10, or 20, or 30, or 40, or 50, or 60, or 70, or 80, or 90, or 100 other servers are pinged, each of which has a static IP address and/or dedicated URL.

In some situations, when the first server is pinged, the network-enabled device sends a ping packet to the first server. Similarly, in some situations, when the second server is pinged, the network-enabled device sends a ping packet to the second server. The ping packet may include one or more predetermined characters or character strings (e.g., "Hello world"). In some cases, the ping packet includes a file with machine-encoded data, such as a media file (e.g., encoded media file).

In some situations, if a response is not received from either or both of the first server and the second server, then the network-enabled device connects to another network provider (e.g., router). The network-enabled device then pings the first and second server, as described above.

In some situations, if a response is received from one or both of the first and second servers, then the network-enabled device connects to a second network provider based on at least one predetermined network connectivity criterion ("network connectivity criterion") selected from the group consisting of the bandwidth of the other network provider, cost to maintain connectivity to the other network provider, cost to transmit information with the aid of the other network provider, the download rate of the other network provider and the upload rate of the other network provider. For instance, the network-enabled device connects to the second network provider if the second network provider enables a higher network bandwidth than the first network provider. In such a case, all connections to first network providers may be terminated. In some situations, the network-enabled device continues to determine whether other network providers may provide a network connectivity that is improved with respect to the second network provider based on one or more network connectivity criteria (or rules) provided herein.

In some embodiments, the network-enabled device maintains connectivity to a network provider if, in response to pinging the first server and the second server, the first server responds to the network-enabled device and/or the second server responds to the network-enabled device. In an embodiment, connectivity is maintained if the first server and the second server both respond to the network-enabled device in response to the network-enabled device pinging the first and second server. In another embodiment, connectivity is maintained if either one of the first server and the second server responds to the network-enabled device. In an example, a response from the first server is sufficient for the network-enabled device to retain connectivity to the first network provider. In some cases, however, the network-enabled device connects to another network provider if the first server does not respond to the network-enabled device and/or the second server does not respond to the network-enabled device.

The network-enabled device may connect to another network provider even if the first server and second server respond to the network-enabled device but one or more network connectivity criteria are not satisfied. In an example, the network-enabled device connects to another network provider if the network bandwidth is below a predetermined limit. In some cases, the network-enabled device connects to another network provider if the network bandwidth is below about 100 kbit/s, or 500 kbit/s, or 1 Mbit/s, or 2 Mbit/s, or 5 Mbit/s, or 10 Mbit/s. In an embodiment, the network-enabled device connects to another network provider if the network bandwidth is below a predetermined limit, such as a user-defined limit.

In an example, if the first server and/or second server do not respond to the network-enabled device, or if one or more network connectivity criteria (e.g., network bandwidth above a predetermined limit) are not met, the network-enabled device connects to a second network provider and sequentially or simultaneously pings the first server and second server with the aid of the second network provider.

In some cases, connecting to the second network provider comprises terminating connectivity to other network providers. Next, the network-enabled device determines whether to maintain connectivity to the second network provider based on whether a response is received by the network device from the first server and/or whether a response is received by the network device from the second server.

In some situations, if the network-enabled device does not receive a response from the second server, the network-enabled device determines that it is not in network communication with a domain name system (DNS) server. This may be due to a malfunctioning DNS server, for example. In some situations, the first server is a domain name system (DNS) server.

In some situations, the second server includes one or more servers for hosting the URL. In an example, the second server is a dedicated server for hosting the URL.

FIG. 1 shows a method 100 for connecting a network-enabled device (also "network device" herein) to a network, in accordance with an embodiment of the invention. In a first step 105, the network device connects to a network provider, such as a wired or wireless network router. Next, in a second step 110, the network device pings a first server having a static IP address. In a third step 115, the network device pings a second server having a static URL. Next, in a fourth step 120, the network device determines whether a response (e.g., ping packet) was received from the first server and the second server. If a response was not received from the first server and the second server, then in a fifth step 125 the network device connects to another network provider, and the method 100 is repeated. If a response was received from the first server and the second server, then in an optional sixth step 130 the network device determines whether one or more network connectivity factors provided herein, such as, e.g., bandwidth, upload rate, and/or download rate, are met. If the one or more network connectivity factors are not met, then the network device connects to another network provider and the method 100 is repeated. However, if the one or more network connectivity factors are met, then in a seventh step 135 the network device maintains the connection (e.g., wired connection, wireless connection) to the network provider. A user operating the network device will then use the network, as desired, such as, for example, to navigate the World Wide Web or send and receive electronic mails.

The network device may connect to another network provider using the same network interface (e.g., WiFi interface) or using another network interface. In an example, in step 105 the network device connects to a WiFi router using a first wireless interface (e.g., WiFi interface) of the network device. Following step 130, the network device connects to a GSM or CDMA provider using a second wireless interface configured to enable the network device to communicate with the GSM or CDMA provider, and the method 100 is repeated using the second wireless interface.

As an alternative to step 120, the network device determines whether a response was received by the second server having the static URL. In such a case, if a response is received, then the network device maintains the connection to the network provider. The response from the first server in such a case may be used for various network diagnostic purposes, such as upload rate and download rate.

As an alternative to or in conjunction with the network-enabled device pinging the first and second servers, establishing connectivity to a network provider includes directing data packets from the network-enabled device to the first server and the second server. In some situations, data packets may be used in place of or in conjunction with ping packets.

In some embodiments, a method for establishing network connectivity for a network device comprises connecting to a network provider and directing a first data packet to a first server having a static internet protocol (IP) address. The first data packet is directed with the aid of the network provider. That is, the network provider brings the network device in communication with the first server. Next, the network device directs a second data packet to a second server having a static uniform resource locator (URL). The second data packet is directed with the aid of the network provider. That is, the network provider brings the network device in communication with the second server. The first and second data packets are directed to the first and second servers, respectively, either sequentially or simultaneously. In some cases the network device directs the second data packet to the second server before directing the first data packet to the first server. Next, the network device determines whether to maintain connectivity to the network provider based upon a comparison of one or more data packets received by the network device from the first server and the second server. In some cases, the comparison comprises performing a checksum to determine the similarity between the data packets received by the network device and the first and second data packets.

Next, the network-enabled device determines whether any data packets were received from the first server and/or second server. In some situations, if no data packet is received by the network device from the first server or the second server, then the network device terminates the connection to the network provider and connects to another network provider, if one is available. A data packet may not be received from the first server and/or the second server for various reasons, such as, for example, a broken link between the network provider and the first and/or second servers, a malfunctioning network, poor network integrity, or dysfunctional first and/or second servers.

In some situations, the first server is a domain name system (DNS) server. In an example, the first data packet and/or the second data packet is an echo request packet.

In some situations, the second server includes one or more servers for hosting the URL. In an example, the second server is a dedicated server for hosting the URL.

In some situations, the network-enabled device (also "network device" herein) directs the first data packet to the first server by first pinging the first server. Upon successfully pinging the first server, the network device directs the first data packet to the first server. Similarly, the network device directs the second data packet to the second server by first pinging the second server. Upon successfully pinging the second server, the network device directs the second data packet to the second server. The network device then determines various network connectivity factors based upon the time taken to receive data packets from the first and second servers, the time taken to upload the first and second data packets to the first and second servers, or whether received data packets match what was transmitted to the first and second servers.

The network device maintains connectivity to the network provider if a first received data packet of the one or more data packets received by the network device is the same as the first data packet directed to the first server. In some situations, however, the network device maintains connectivity if the first received data packet is at least about 1%, or 5%, or 10%, or 15%, or 20%, or 25%, or 30%, or 35%, or 40%, or 45%, or 50%, or 55%, or 60%, or 65%, or 70%, or 75% or 80%, or 85%, or 90%, or 95%, or 99% similar to the first data packet. Such similarity may be assessed by comparing the data packets to one another, such as, for example, by comparing character strings to one another if the data packets are character strings.

Similarly, the network device maintains connectivity to the network provider if a second received data packet of the one or more data packets received by the network device is the same as the second data packet directed to the second server. In some situations, however, the network device maintains connectivity if the second received data packet is at least about 1%, or 5%, or 10%, or 15%, or 20%, or 25%, or 30%, or 35%, or 40%, or 45%, or 50%, or 55%, or 60%, or 65%, or 70%, or 75% or 80%, or 85%, or 90%, or 95%, or 99% similar to the second data packet.

A connection to the network provider may be maintained if a checksum of the first received data packet matches a predetermined data packet. In an example, connectivity is maintained if the first received data packet matches a predetermined string (e.g., "Hello world"). In other situations, connectivity to the network provider is maintained if a checksum of the second received data packet matches a predetermined data packet. As an alternative, connectivity to the network provider is maintained if the first data packet matches the first received data packet and/or the second data packet matches the second received data packet. In some cases, connectivity is maintained if both the first and second data packets match the first and second received data packets, respectively.

In some situations, if the first received data packet is different from the first data packet and/or the second received data packet is different from the second data packet, the network-enabled device (also "network device" herein) connects to another network provider. In an example, the network device searches for, finds and connects to another network provider, such as another wireless router.

One or both of the first and second data packets may be used to determine an upload and download rate of the network provided by the network provider. In an example, the network-enabled device uses the rate at which the first data packet is uploaded to the first server and downloaded from the first server and/or a rate at which the second data packet is uploaded to the second server and downloaded from the second server to determine an upload rate and download rate, which may be an averaged upload rate and download rate for the network. For example, the upload rate is averaged using the upload rate(s) to the first and second servers and the download rate is averaged using the download rate(s) from the first and second servers. This may in turn enable the network-enabled device to determine whether to maintain connectivity to the network provider or connect to another network provider.

If no network access is provided by the network provider or if network access provided by the network provider does not meet one or more network connectivity criteria or factors (e.g., upload rate, download rate, or network cost), then the network device connects to another network provider and repeats the methods outlined above. In an example, if the network device connects to another network provider, the network device directs the first data packet to the first server and the second data packet to the second server. The first and second data packets are directed (or sent to) the first and second servers, respectively, with the aid of the other network provider. In such a case, the network device also determines whether to maintain connectivity to the other network provider based upon a comparison of one or more data packets received by the network device from the first server and the second server, as described above.

In some cases, upon connecting to another network provider the network device terminates its connection to other network providers. In other cases, however, the network device maintains its connection (or connectivity) to one or more other network providers. This may enable the network device to find and establish improved network connectivity if and when it becomes available.

Figure 2:
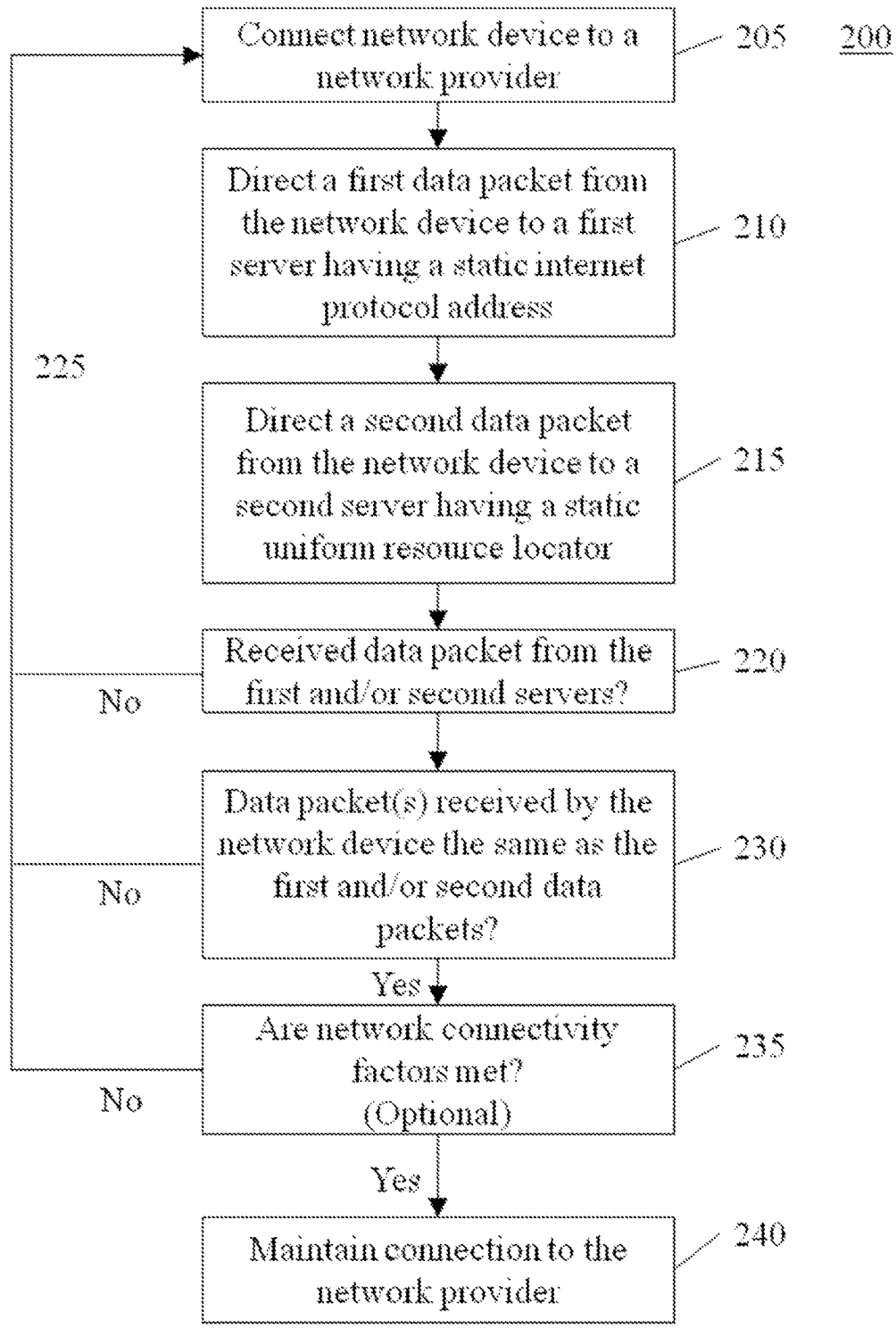
FIG. 2 shows a method for connecting a network device to a network, in accordance with an embodiment of the invention.

FIG. 2 shows a method 200 for connecting a network-enabled device (also "network device" herein) to a network, in accordance with an embodiment of the invention. In a first step 205, the network device connects to a network provider, such as a wired or wireless network router. Next, in a second step 210, the network device directs a first data packet to a first server having a static IP address. In a third step 215, the network device directs a second data packet to a second server having a static URL. Next, in a fourth step 220, the network device determine whether any data packets were received from the first server and/or second server. The network device may continually monitor for any received data packets or monitor at predetermined intervals, such as ever 1 second, 10 seconds, 30 seconds, 1 minute, 5 minutes, or 10 minutes. In some cases, if no data packets are received, then in a fifth step 225 the network device connects to another network provider and the method 200 is repeated. In other cases, if a data packet is received from at least one of the first server and the second server, then in a sixth step 230 the network device determines whether the data packet received by the network device is the same as either the first or second data packet. In an example, if a first received data packet is received by the network device from the first server and a second received data packet is received by the network device from the second server, then the network device determines whether the first received data packet is the same as the first data packet and whether the second received data packet is the same as the second data packet. If the data packets are not the same, then the network device connects to another network provider and the method 200 is repeated.

In an embodiment, connectivity to the network provider is maintained if at least one received data packet is the same as either the first or second data packet. In another embodiment, connectivity to the network provider is maintained if the first received data packet from the first server is the same as the first data packet, and the second received data packet from the second server is the same as the second data packet.

In some situations, in a seventh step 235 the network device determines whether one or more network connectivity factors provided herein, such as, e.g., bandwidth, upload rate, and/or download rate, are met when the network device accesses the network through the network provider. In some cases, if the one or more network connectivity factors are not met, then the network device connects to another network provider and the method 200 is repeated. However, if the one or more network connectivity factors are met, then in an eighth step 240 the network device maintains the connection (e.g., wired connection, wireless connection) to the network provider. A user operating the network device may then use the network, as desired.

In some embodiments, connecting to a network provider first entails locating the network provider in a search location. In an embodiment, the search location is a predetermined location determined by a user of the network-enabled device. The predetermined location may be a business or residential location, or public location (e.g., park, street). In another embodiment, the search location is within a predetermined radius from a location of the user. In some situations, the search location has a radius of at least about 1 meter ("m"), or 2 m, or 3 m, or 4 m, or 5 m, or 6 m, or 7 m, or 8 m, or 9 m, or 10 m, or 20 m, or 30 m, or 40 m, or 50 m, or 60 m, or 70 m, or 80 m, or 90 m, or 100 m, or 200 m, or 300 m, 400 m, or 500 m, or 600 m, or 700 m, or 800 m, or 900 m, or 1000 m, or 2000 m, or 3000 m, or 4000 m, or 5000 m. In some cases, the search location is determined by the user or updated by the network device as the user changes his or her location.

In some cases, once a network-enabled device has connected to a network provider, the network-enabled device determines whether to maintain connectivity to the network provider based on one or more network connectivity criteria selected from the group consisting of network bandwidth ("bandwidth"), cost to maintain connectivity to the network provider, cost to transmit information with the aid of the network provider, the download rate and the upload rate. In some situations, the network-enabled device makes a similar determination as to another network provider and connects to the other network provider if improved network conditions are provided by the other network provider.

In one example, the network device connects to a first network provider (e.g., wireless router) and pings a the first server (with a static IP address) and second server (with a dedicated URL). Upon receiving a response from the first and second servers, the network device determines whether network access via the first network provider is optimum (or preferable) by calculating an upload rate and download rate of the network provided by the first network provider. If the upload and download rates are above a predetermined limit, the network device maintains its connection to the first network provider and a user may access the network through the first network provider. In some cases, the network device also connects to a second network provider and pings the first and second servers. Connection to the second network provider may be made while the network device is still connected to the first network device. Alternatively, the network device may terminate its connection to the first network provider and connect to the second network provider. Upon receiving a response from the first and second servers, the network device determines whether network connectivity via the second network provider is optimum by calculating an upload rate and download rate of the network provided by the first network provider. If the upload and download rates are improved with respect to the upload and download rates provided by the first network provider, then the network device terminates its connection to the first network provider and maintains (or establishes) its connection to the second network provider.

In some situations, when the network-enabled device has the option of using multiple network providers (e.g., two, five or ten network providers), such as a first or second network provider, to connect to the network, the network-enabled device uses the second network provider if the network-enabled device determines that network conditions using the second network provider are optimum, improved or preferable as compared to network conditions using the first network provider. This scenario may be relevant if the network-enabled device has pinged the first and second server with the aid of the first and second network providers and in both cases a response was received by the network-enabled device. The network-enabled device uses the second network device (as opposed to the first network device) based upon a determining at least one network connectivity criterion selected from the group consisting of the bandwidth of the second network provider, cost to maintain connectivity to the second network provider, cost to transmit information with the aid of the second network provider, the download rate of the second network provider, the upload rate of the second network provider and mode of connectivity (i.e., wired connectivity or wireless connectivity). As an example, if the network-enabled device determines that the cost for connecting to and using the network via the second network provider is lower than the cost for connecting to and using the network via the first network provider, the network-enabled device accesses the network via the second network provider. As another example, if the network-enabled device determines that the network bandwidth via the second network provider is greater than the network bandwidth via the first network provider, then the network-enabled device accesses the network via the second network provider. As another example, if network access via the second network provider is through a wired connection and network access via the first network provider is through a wireless connection, and wired connections are preferable over wireless connection, then the network-enabled device accesses the network via the second network provider.

In some embodiments, a method for establishing network connectivity for a network device comprises connecting to a network provider and pinging, with the aid of the network provider, a first server having a static internet protocol (IP) address and/or a second server having a static (or dedicated) uniform resource locator (URL). Next, a connection to the network provider is terminated based upon any one network termination condition selected from the group consisting of (a) a response was not received by the network device from the first server and/or the second server after pinging, (b) a network bandwidth of another network provider is higher than a network bandwidth of the network provider, (c) a network cost of another network provider is lower than a network cost of the network provider, (d) network access provided by another network provider is more robust than network access provided by the network provider, (e) connectivity between the network device and another network provider is via wired connection and connectivity between the network device and the network provider is via wireless connection and (f) another network provider is in closer proximity to the network device than the network provider. In some situations, the connection to the network provider is terminated based upon any two, or any three, or any four, or any five network termination conditions selected from the group. In other situations, the connection to the network provider is terminated based upon all network termination conditions.

Connectivity between the network device and the first network provider is via a wired or wireless network access point. That is, in some cases connectivity between the network device (also "network-enabled device" herein) is through a wired connection (e.g., coax, opto-electronic) to the first network provider, and in other cases connectivity is through a wireless connection (e.g., WiFi, Bluetooth) to the first network provider. Network providers are connected to a network, such as one or more servers providing network access to the World Wide Web, via wired or wireless connections to one or more machines with access to the network.

In some embodiments, a method for establishing network connectivity for a network device, comprises connecting a network device to a first network provider. Next, with the aid of the first network provider, the network device pings a first server and a second server. In some situations, one or both of the first and second servers have a static IP addresses. In other situations, one or both of the first and second servers have static URLs. In other situations, the first server has a static IP address and the second server has a static URL.

Next, the network device terminates its connection to the first network provider and subsequently (or simultaneously) establishes a connection to a second network provider if the second network provider meets one or more criteria unmet by the first network provider. In an embodiment, the one or more criteria are selected from the group consisting of (a) whether a response was received by the network device from the first server and/or the second server after pinging, (b) whether a network bandwidth of the second network provider is higher than a network bandwidth of the first network provider, (c) whether a network cost of the second network provider is lower than a network cost of the first network provider, (d) whether network access provided by the second network provider is more robust than network access provided by the first network provider, (e) whether connectivity between the network device and the second network provider is via wired connection and connectivity between the network device and the first network provider is via wireless connection, and (f) whether the second network provider is in closer proximity to the network device than the first network provider.

In some situations, the connection between the network device and the first network provider is terminated if, in response to the network device pinging the first server and second server, a response is not received by the network device from the first server or the second server. Alternatively, the connection is terminated if a response is not received by the network device from the first server and the second server.

In some cases, a method for establishing network connectivity for a network-enabled device, comprises the network-enabled device connecting to a first network provider (e.g., wireless router) and locating a second network provider. The second network provider has a higher ranked order of preference than the first network provider based on one or more predetermined network connectivity criteria. For example, the second network provider has a higher network bandwidth than the first network provider. Next, the network-enabled device connects to the second network provider. The one or more predetermined network connectivity criteria is selected from the group consisting of network bandwidth, network cost, and proximity of the network device to a network provider.

In some cases, the network-enabled device selects network providers from a list of network providers generated by the network-enabled device. The list may include network providers within a predetermined location or within a predetermined search radius, such as a radius of at least about 1 meter ("m"), or 2 m, or 3 m, or 4 m, or 5 m, or 6 m, or 7 m, or 8 m, or 9 m, or 10 m, or 20 m, or 30 m, or 40 m, or 50 m, or 60 m, or 70 m, or 80 m, or 90 m, or 100 m, or 200 m, or 300 m, or 400 m, or 500 m, or 600 m, or 700 m, or 800 m, or 900 m, or 1000 m, or 2000 m, or 3000 m, or 4000 m, or 5000 m. Network providers may be ranked by order of preference, which is determined on the basis of network connectivity factors. Alternatively, network providers may be ranked on the basis of whether a response is received by the network-enabled device upon pinging the first and/or second server. A network provider at the top of the list may have received a response from both the first and second servers whereas a network provider at the bottom of the list might not have received a response from either the first or second server. The ranking may be a weighed ranking. In some cases, the ranking may be weighed with the aid of network connectivity factors. In an example, the ranking is weighted on the basis of network bandwidth—i.e., un-weighted rank order×network bandwidth/total network bandwidth summed across all network providers in the list.

The rank order may be saved in a storage location of the network-enabled device such as a data file or memory location, and updated manually by a user or at a predetermined interval, such as every 1 or more second, or 2 or more second, or 3 or more second, or 4 or more second, or 5 or more second, or 10 or more seconds, or 30 or more seconds, or 1 or more minutes, or 5 or more minutes, or 10 or more minutes, or 30 or more minutes, or 1 or more hours, or 12 or more hours, or 1 or more days.

In an example, the first network provider has a higher ranked order of preference than the second network provider if the first network provider enables a higher network bandwidth than the second network provider. The network device connects to the first network provider from the list but continually or intermittently determines whether network connectivity is optimum or more preferable network access is provided by another network provider. If network access through the second network provider is preferable with respect to the first network provider, such as if the second network provider offers cheaper internet access or higher network bandwidth, then the network device terminates the connection to the first network provider and connects to the second network provider.

In an embodiment, the network device connects to a network provider only if the network device successfully pings a first server and a second server (i.e., a response is received by the network provider after pinging the first and second servers). In an embodiment, the first server has a static internet protocol (IP) address and the second server has a static (or dedicated) uniform resource locator (URL).

In some situations, the second network provider is located by searching for other network providers within a predetermined or user-selected search radius of at least about 1 meter ("m"), or 2 m, or 3 m, or 4 m, or 5 m, or 6 m, or 7 m, or 8 m, or 9 m, or 10 m, or 20 m, or 30 m, or 40 m, or 50 m, or 60 m, or 70 m, or 80 m, or 90 m, or 100 m, or 200 m, or 300 m, or 400 m, or 500 m, or 600 m, or 700 m, or 800 m, or 900 m, or 1000 m, or 2000 m, or 3000 m, or 4000 m, or 5000 m. The network device then generates a list of network providers within the search radius.

Figure 3:
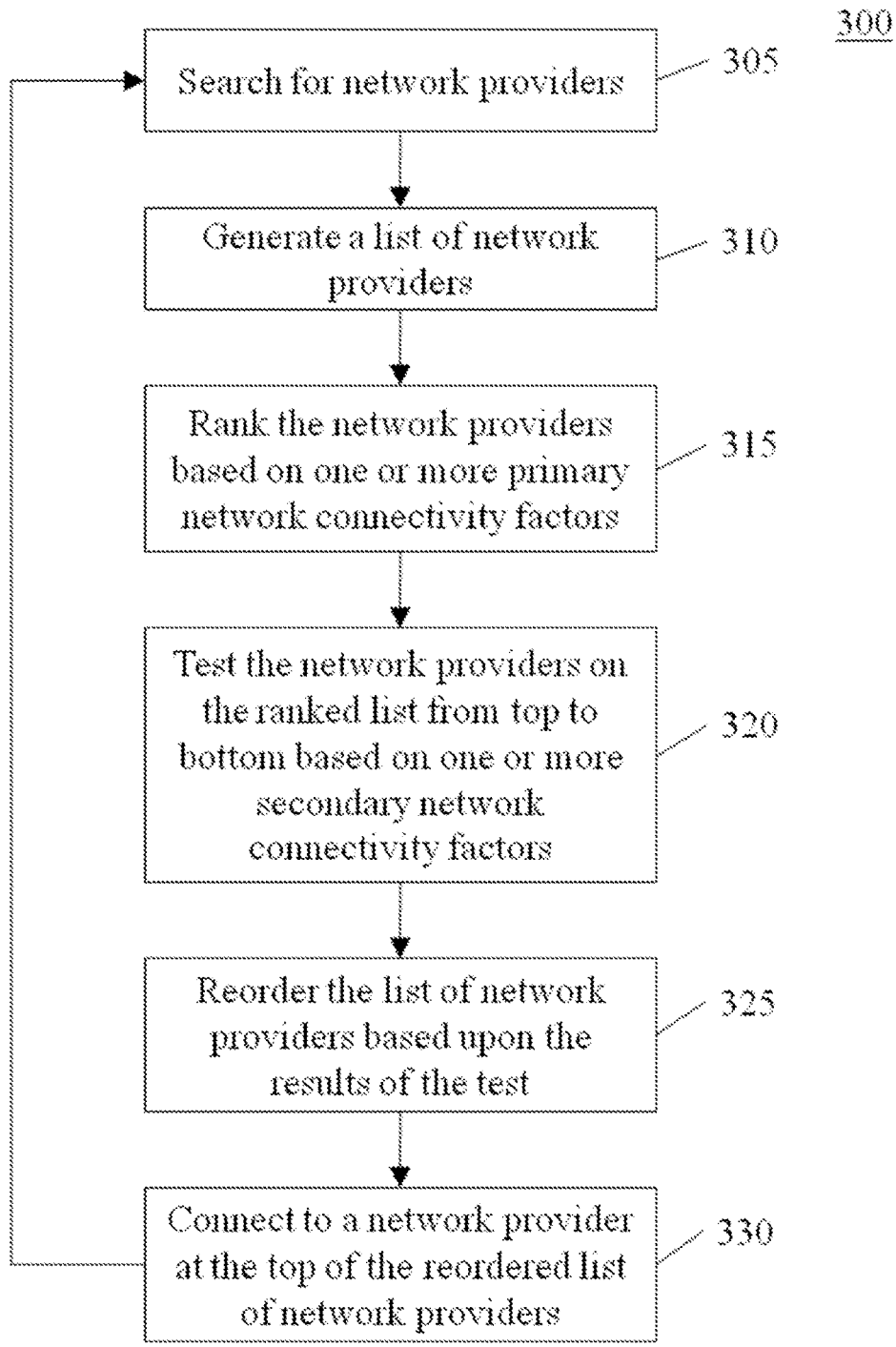
FIG. 3 shows a method for generating a ranked list of network providers, in accordance with an embodiment of the invention.

FIG. 3 shows a method 300 for generating a ranked list of network providers, in accordance with an embodiment of the invention. In a first step 305, the network-enabled device searches for network providers (e.g., WiFi access points, 2G network, 3G network, 4G network). In an embodiment, the search is within a predetermined search radius, such as a radius of at least about 1 meter ("m"), or 2 m, or 3 m, or 4 m, or 5 m, or 6 m, or 7 m, or 8 m, or 9 m, or 10 m, or 20 m, or 30 m, or 40 m, or 50 m, or 60 m, or 70 m, or 80 m, or 90 m, or 100 m, or 200 m, or 300 m, or 400 m, or 500 m, or 600 m, or 700 m, or 800 m, or 900 m, or 1000 m, or 2000 m, or 3000 m, or 4000 m, or 5000 m. In another embodiment, the search radius is a user-selected search radius. In another embodiment, the search is within a predetermined or user-selected location, such as a building (e.g., shopping mall, school).

Next, in a second step 310, the network-enabled device generates a list of network providers based on the search conducted in the first step 305. In a third step 315, the network-enabled device ranks the network providers based on one or more primary network connectivity factors. In an embodiment, the one or more primary network connectivity factors are selected from the group consisting of bandwidth, cost to maintain connectivity to the network provider, cost to transmit information with the aid of the network provider, the download rate, the upload rate, and whether a ping packet is received from a first server and/or whether a ping packet is received from a second server (see above). In an example, a network provider offering network connectivity at a lower cost than another network provider has a higher rank. In another embodiment, the one or more network connectivity factors include proximity to network providers. In such a case, a network provider that is close to the network-enabled device (as measured by the signal strength, for example) has a higher rank than another network provider that is further away from the network-enabled device. The network-enabled device generates a ranked list based on the one or more primary network connectivity factors.

In an alternative embodiment, in the third step 315 the ranked list of network providers is generated by assigning the one or more network providers on the list generated in the second step 310 a random position. This is accomplished with the aid of a random number generator or pseudo random number generator. In such a case, a network provider that would otherwise have a lower rank than another network provider may appear at the top of the ranked list of network providers. As another alternative, the list of network providers in the second step 310 is populated in the order in which network providers are identified by the network-enabled device and the third step 315 is precluded. In an example, the list of network providers is populated in the order in which the network providers respond to the network-enabled device, such as, for example, the network-enabled device pinging the network providers. In such a case, the first to respond is first on the list, the second to respond is second on the list, and so on. In another example, the list of network providers is populated in the order in which the network-enabled device receives some identifiable material from the network providers. The identifiable material includes text or other data that permits the network-enabled device to identify each of the network providers.

Next, in a fourth step 320, the network-enabled device tests the network providers on the ranked list based on one or more secondary network connectivity factors. The one or more secondary network connectivity factors are selected from the group consisting of bandwidth, cost to maintain connectivity to the network provider, cost to transmit information with the aid of the network provider, the download rate, the upload rate, and whether a ping packet is received from a first server and/or whether a ping packet is received from a second server (see above). In an example, if the ranked list is randomly populated, then the secondary network connectivity factors aid in refining the list to identify preferable or more preferable network providers. A network provider may be preferable if, for example, the network provider provides an upload rate, download rate and/or a network bandwidth ("bandwidth") at or above a predetermined limit or greater than other network providers on the ranked list.

Next, in a fifth step 325, the network-enabled device reorders the list of network providers based upon the results of the test in the fourth step 320. In some situations, testing the network providers based on one or more secondary network connectivity factors does not result in any reordering of the list generated in the second step 310 and third step 315.

In a sixth step 330, the network-enabled device connects to a network provider at the top of the reordered list as generated in the fifth step 325. In some situations, the method 300 is repeated to continually or periodically update the list of network providers such that the most preferable network provider is at the top of the list. In an example, if the order of the network providers changes, the network-enabled device connects to a new network provider at the top of the list. In other situations, the method 300 is repeated manually, such as by request from a user operating the network-enabled device.

In an embodiment, the network-enabled device stores lists of network providers in a list or data file in memory, cache, or other storage location (e.g., hard disk) of the network-enabled device. In other embodiments, the network-enabled device stores the lists of network providers on a server. In some cases, the list is continually updated and the server includes the most up-to-date list of network providers. If the network-enabled device has a global positioning service (GPS) feature or is able to triangulate its location, then providing the location of the network-enabled device with the list of network providers enables generation of a map of preferable network providers as a function of location.

Network Connectivity Criteria

Another aspect of the invention provides network connectivity criteria (or rules). Such rules can be used to determine which network provided to employ for network access. For instance, a rule may specify that a network provider will be selected on the basis of upload and download rates. In such a case, a network-enabled device connects to a network provider and pings a first serer having a static IP address and a second server having a static URL. This is repeated for any other network providers. A list of network providers is generated having network provides that enabled the network-enabled device to successfully ping the first and second servers. From the list, the network-enabled device selects the network provider that provides the highest upload and download rates.

In some embodiments, network connectivity rules are selected from a bandwidth of the another network provider, cost to maintain connectivity to the another network provider, cost to transmit information with the aid of the another network provider, a download rate of the another network provider and an upload rate of the another network provider.

In some embodiments, network connectivity rules include (a) whether a response was received by the network device from the first server and the second server after pinging the first server and the second server, (b) whether a network bandwidth of the second network provider is higher than a network bandwidth of the first network provider, (c) whether a network cost of the second network provider is lower than a network cost of the first network provider, (d) whether network access provided by the second network provider is more robust than network access provided by the first network provider, (e) whether connectivity between the network device and the second network provider is via wired connection and connectivity between the network device and the first network provider is via wireless connection, and (f) whether the second network provider is in closer proximity to the network device than the first network provider.

Network connectivity rules may be stored on a network location accessible by a network-enabled device or stored in a storage location (e.g., memory, hard disk, cache) of the network-enabled device. Network connectivity rules may be updated manually or at predetermined times, such as at predetermine intervals (upon a system or software update, for example). Network connectivity rules in some cases are user-defined. In such a case, a user modifies network connectivity rules of the user's network-enabled device. In an example, a user defines a rule prescribing that network connectivity is established using a network provider that enables the fastest network access and the lowest network cost.

In some embodiments, network connectivity rules (or criteria) are dynamic. In an embodiment, network connectivity rules may vary with a location of a network-enabled device. In an example, network connectivity rules in a first geographic location (e.g., New York, the United States of America) are different from network connectivity rules in a second geographic location (e.g., Paris, France).

In some situations, a network-enabled device determines a location of the network enabled device with the aid of a global positioning system, such as global positioning service (GPS), and loads or downloads network connectivity rules for use at the location. In some cases, the network-enabled device loads preset (or default) rules and subsequently updates the rules with location-specific rules once network access has been established using the default rules. The default rules may be stored on the network-enabled device.

Location-specific (location-based) rules may enable a user to optimize network connectivity at various geographic locations. Network access in one location may be optimized using a set of rules that are different for optimizing network access in another location. As an example, network access in Paris may be optimum with the aid of a GSM provider than a CDMA provider, even though a network-enabled device may be able to access a network through either the GSM or CDMA provider. This may be the case if, for example, a user has a plan with the GSM provider but not the CDMA provider.

In some cases, rules may be time-based rules. Time-based rules provide rules that vary as a function of time, such as time of day, day of week, week of month, month of year, and so on. In some cases, a network-enabled device uses one or more morning rules for testing network connectivity in the morning, one or more afternoon rules for testing network connectivity in the afternoon, and one or more evening rules for testing network connectivity in the evening. Morning, afternoon and evening rules may vary based on the cost of network access, the upload rate and/or the download rate for these time periods.

In some cases, rules may be bandwidth-based rules in which rules may vary based on a predetermined level of bandwidth accessible to the network-enabled device. For instance, if a network-enabled device has exhausted its prescribed bandwidth through a network provider, then a network connectivity rule may require that the network-enabled device use another network provider. Some rules may require certain network connectivity guidelines based on the bandwidth (i.e., available or consumed data) available to a network-enabled device. In an example, if a network device has not exhausted its allotted bandwidth (e.g., 10 gigabits per month) through a first network provider, then the network device will use the first network provider; however, if the network device has exhausted its allotted bandwidth, then the network device will use a second network provider. This may be useful if the network device will incur excess usage charges if the network device uses the first network provider.

In some embodiments, a network-enabled device connects to a network through a peer device, such as another network-enabled device. Thus, the peer device may behave as a network provider. In such cases, the network-enabled device has rules that may require the network-enabled device to connect to the peer device when certain conditions are met, such as when network connectivity is preferable through the peer device then through connectivity via a network provider. This may be the case if, for example, the network-enabled device has exhausted its allotted bandwidth (or other usage restrictions) for a particular network provider, and network connectivity through that network provider would be cost-prohibitive.

Figure 6:
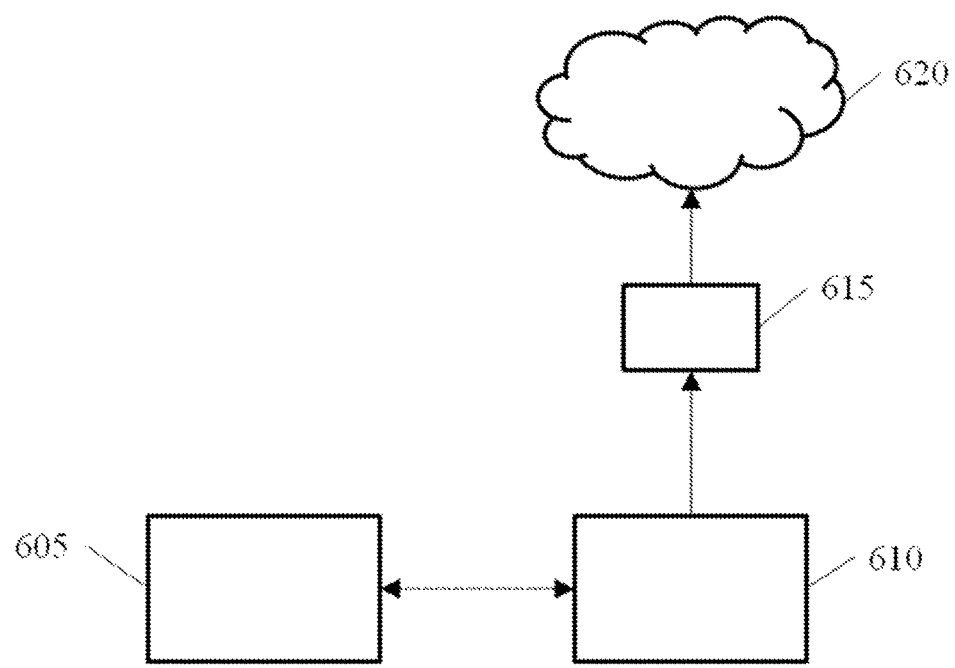
FIG. 6 shows a first network-enabled device communicating with a second network-enabled device, in accordance with an embodiment of the invention.

FIG. 6 shows a first network-enabled device 605 and a second network-enabled device 610. The second network-enabled device 610 has connected to a network provider 615 that in turn is connected to a network 620, such as an intranet or the Internet. The connection may be through a wired or wireless network interface of the first network-enabled device 605 and the second network-enabled device 610. In the illustrated example, the connection is through a wireless interface of the first network-enabled device 605 and the second network-enabled device 610; the connection between the first network-enabled device 605 and the second network-enabled device 610 is wireless (dashed two-way arrow). The second network-enabled device 610, in some cases, has successfully pinged a first server having a static IP address and a second server having a static URL. In addition, the second network-enabled device 610 may have satisfied certain network connectivity rules, such as geographic-based rules (e.g., the second network-enabled device 610 has selected the network provider 615 based on the geographic location of the second network-enabled device 610).

In some embodiments, a network-enabled device connects to a network provider (e.g., a router or a peer device) that is a trusted network provider—i.e., the network-enabled device trusts the network provider. Such trust may be established with the aid of a trust protocol. For instance, a user may generate a list of trusted network providers, or the user's network-enabled device may maintain a record of network providers that the user has previously selected for use.

In other situations, the trust protocol may be provided through a system having one or more servers that provide trust protocols to a network-enabled device. Such trust protocols may be location-based. The trust protocols may be included in the connectivity rules of the network-enabled device, which may be manually or periodically updated.

In some embodiments, a first network-enabled device may communicate with a network (intranet or the Internet) by connecting to a second network-enabled device that is communicatively coupled to the network. The second network-enabled device in such a case may have connected to a network-provided and successfully pinged a first sever having a static IP address and a second server having a static URL. The first network-enabled device may, in turn, provide network connectivity to a third, fourth, or more network-enabled devices. In some cases, the first network-enabled device may received updates (e.g., rules update, software update) from the network via the network connectivity of the second network-enabled device.

Network Credits

In another aspect of the invention, network credits are provided for enabling a network-enabled device to connect to a network through a peer device (e.g., another network-enabled device) that has connected to the network. In some embodiments, network credits provide a network-enabled device an incentive to provide network connectivity for another network-enabled device; the other network-enabled device in such cases may prefer network connectivity through the peer device over a non-peer device type of network provider (e.g., router).

In an example, a first network-enabled device connects to a second network-enabled device that has successfully connected to a network through a router (e.g., WiFi connection or connection through a CDMA access point). In some cases, network connectivity for the first network-enabled device through the second network-enabled device may be preferable if it is cheaper than connectivity through a non-peer device type of network provider, or if the second network-enabled device provides a preferable signal or bandwidth in comparison to the non-peer device type of network provider. This may be the case if the first network-enabled device has exhausted its allotted bandwidth through a particular network provider, such as the router to which the second network-enabled device is connected. In exchange for providing network connectivity to the first network-enabled device, the second network-enabled device receives from the first network-enabled device network credits.

In some embodiments, network credits provide network-enabled devices an incentive to connect to a network through peer-to-peer connectivity (see, e.g., FIG. 6). In an embodiment, network credits are a promise for future payment, such as at a predetermined rate or a rate that is agreed to by users of network-enabled device at the time of peer-to-peer connectivity. In another embodiment, network credits are a promise for future network use. In such a case, if a first network-enabled device pays a second network-enabled device for network access using network credits from the first network-enabled device, the first network-enabled device may provide the second network-enabled device network access at a future point in time.

Network credits may be negotiated between network-enabled devices to capture access use restrictions, such as bandwidth and usage time. For instance, if a first network-enabled device pays a second network-enabled device for network access using network credits, the network credits may provide the second network-enabled device a certain bandwidth (e.g., 2 megabits/second for 30 minutes) of the first network-enabled device at a future point in time. Alternatively, the network credits may be the promise for a payment of a predetermined or negotiated sum of money. In some embodiments, the predetermined or negotiated sum of money is lower than the cost of network connectivity through a non-peer device type of network provider.

Network Connectivity Systems

In another aspect of the invention, a system for establishing network connectivity for a network device comprises a network connectivity system configured to locate network providers. The network connectivity system is configured to establish a connection to a network provider, ping a first server having a static internet protocol (IP) address with the aid of the network provider, ping a second server having a static uniform resource locator (URL) with the aid of the network provider, and determine whether to maintain connectivity to said network provider based on whether a response was received by said network device from said first server and/or whether a response was received by said network device from said second server.

In some cases, the network connectivity system is part of an electronic device, such as a portable electronic device, or associated with an electronic device. The network connectivity system may be a sub-system of a larger system. In an example, the network connectivity controller is a network card and associated software in a portable electronic device. In another example, the network connectivity controller is a stand-alone system configured to provide network connectivity to electronic devices.

The network connectivity system includes one or more devices selected from the group consisting of central processing unit (CPU), memory (e.g., flash memory), transmitter, and a bus (e.g., serial bus). The transmitter may be a radiofrequency ("RF") transmitter or opto-electronic transmitter. The one or more devices or components may be interconnected, such as by way of a circuit in the network connectivity system, or a system board (e.g., motherboard).

Figure 4:
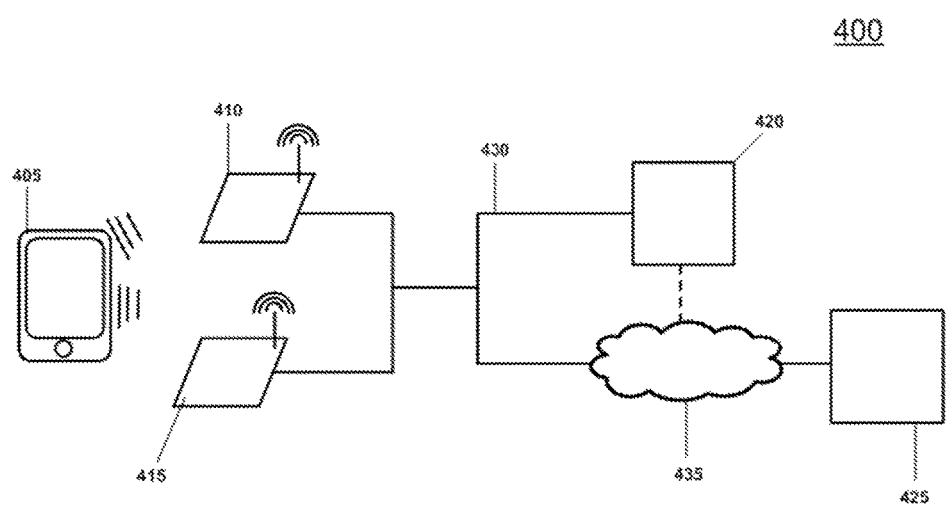
FIG. 4 shows a system having an electronic device and network providers, in accordance with an embodiment of the invention.

FIG. 4 shows a system 400 having an electronic device 405, a first network provider 410, second network provider 415, a first server 420 and a second server 425, in accordance with an embodiment of the invention. The first server 420 is in communication with the first network provider 410 and second network provider 415 through a first network 430, such as an intranet or the Internet 435. The second server 425 is in communication with the first network provider 410 and second network provider 415 through a second network, such as the Internet 435. The first server 420 may be connected to the Internet 435.

The electronic device 405 includes a network connectivity system for connecting the electronic device 405 to the first network provider 410 and pinging the first server 420 and second server 425 or directing a first data packet to the first server 420 and a second data packet to the second server 425, as described above. The network controller includes computer-executable commands (see below) for facilitating various methods described herein.

In some cases, The electronic device 405 is a portable electronic device, such as a laptop computer, tablet PC or Smart phone. In other cases, the electronic device 405 is a stationary electronic device, such as a desktop computer or server. The electronic device 405 may connect to the first network provider 410 and second network provider via wired or wireless modes of communication. As illustrated, the electronic device 405 communicates with the first network provider 410 and second network provider via wireless communication.

The first network provider 410 and second network provider 415 are wireless routers. In other cases, the first network provider 410 and/or second network provider 415 is a wired router or other device configured to bring the electronic device 405 in communication with the network 435. In addition, the system 400 may include other network providers in communication with the network 435.

In an example, the electronic device 405 connects to the first network provider 410 and pings the first server 420 and second server 425. If the electronic device 405 receives a response from the first server 420 and second server 425, the electronic device 405 maintains its connection to the first network provider and a user may access the Internet 435. Otherwise, the electronic device 405 connects to the second network provider 410 and pings the first server 420 and second server 425 and awaits a response.

In cases in which a response is received from both the first server 420 and second server 425, such as via the first network provider 410, the electronic device 405 may determine whether to maintain connectivity to the first network provider 410 in view of various network connectivity factors provided herein. For example, the electronic device 405 terminates connectivity to the first network provider 410 and connects to the second network provider 415 if the network speed of the first network provider 410 is below a predetermined limit (e.g., 100 kbit/s).

Figure 5:
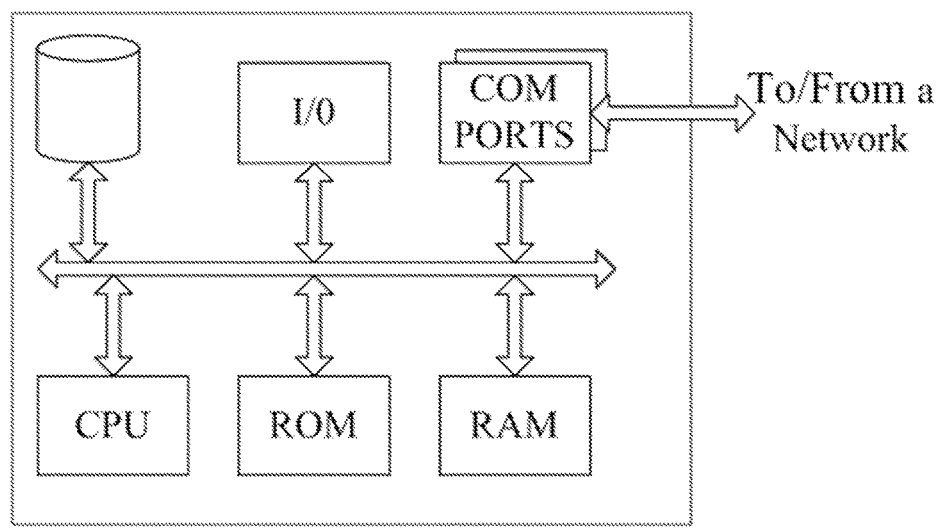
FIG. 5 shows a functional block diagram illustration of general purpose computer hardware platforms, in accordance with an embodiment of the invention.

The electronic device 405, or components (e.g., network controllers) of the electronic device 405, may include random-access memory (RAM) for enabling rapid transfer of information to and from a central processing unit (CPU), and to and from a storage module, such as one or more storage units, including magnetic storage media (i.e., hard disks), flash storage media and optical storage media. Additionally, the system may include one or more storage units, one or more CPUs, one or more RAMs, one or more read-only memories (ROMs), one or more communication ports (COM PORTS), one or more input/output (I/O) modules, such as an I/O interface, a network interface for enabling the system to interact with an intranet, including other systems and subsystems, and the Internet, including the World Wide Web. The storage unit may include one or more databases, such as a relational database. In some cases, the system further includes one or more of a data warehouse for storing information (e.g., network providers, network connectivity history) and a relational database. FIG. 5 shows a functional block diagram illustration of general purpose computer hardware platforms configured for use with methods and systems provided herein.

The electronic device 405, for example, includes a data communication interface for data packet communication and/or pining other systems, such as a server. In some situations, the electronic device 405 includes a central processing unit (CPU), in the form of one or more processors, for executing program instructions. The electronic device 405 may include an internal communication bus, program storage and data storage for various data files to be processed and/or communicated by the system, although the system may receive programming and data via network communications. The hardware elements, operating systems and programming languages of such devices are conventional in nature, and it is presumed that those skilled in the art are adequately familiar therewith. Of course, device functions may be implemented in a distributed fashion on a number of similar platforms, to distribute the processing load (see below). Electronic devices and systems provided herein may include subsystems and modules for distributing and/or allocating tasks.

In some embodiments, the electronic device 405 includes a network controller having a processor for executing methods provided above. The processor is configured to execute machine-readable code (source code or compiled object code) to facilitate methods described in various embodiments of the invention.

In some embodiments, the device 405 includes a user interface for displaying a list having one or more network providers to a user. The user interface in some cases is a graphical user interface (GUI). In an embodiment, the GUI shows a ranked list of network providers, with a more preferable network provider at the top of the list. In another embodiment, the GUI enables a user to select a network provided from the list of network providers. In some situations, the list of network providers is generated with the aid of one or more network connectivity criteria, as described above.

Hence, aspects of the methods outlined above may be embodied in programming. Program aspects of the technology may be thought of as "products" or "articles of manufacture" typically in the form of executable code and/or associated data that is carried on or embodied in a type of machine readable medium. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Media that may bear the software elements include optical, electrical and electromagnetic waves, such as used across physical interfaces between local devices, through wired and optical landline networks and over various air links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

A machine readable medium may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications.

Common forms of computer-readable media therefore include, for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Methods steps may be implemented by a program product, including machine-executable instructions, such as program code, for example, in the form of program modules executed by systems or machines in networked environments. Generally, program modules may include routines, programs, objects, components, data structures, etc., that perform particular tasks or implement particular abstract data types. Machine-executable instructions, associated data structures and program modules represent examples of program code for executing steps of the methods disclosed herein. The particular sequence of such executable instructions or associated data structures represent examples of corresponding acts for implementing the functions described in such steps.

In some situations, systems and methods provide herein are practiced in a networked environment using logical connections to one or more remote computers having processors. Logical connections may include, for example, a local area network (LAN) and/or a wide area network (WAN). Such networking environments may be found in office-wide or enterprise-wide computer networks, intranets and the Internet, and may use a wide variety of different communication protocols. Those skilled in the art will appreciate that such network computing environments may encompass many types of computer system configurations, including personal computers, hand-held devices, multiprocessor systems, microprocessor-based or programmable consumer electronics, network personal computers (PCs), servers, minicomputers, mainframe computers, and the like.

It should be noted that although the flowcharts provided herein (e.g., FIGS. 1 and 2) show a specific order of method steps (also "steps" herein), it is understood that the order of these steps may differ from what is depicted. Also two or more steps may be performed concurrently or with partial concurrence. Such variation may depend on the software and hardware systems chosen, and on designer choice. It is understood that all such variations are within the scope of the invention. Likewise, software and web implementations of the present invention could be accomplished with standard programming techniques with rule based logic and other logic to accomplish the various database searching steps, correlation steps, comparison steps and decision steps.

EXAMPLES

Example 1

A user is in an area with three WiFi routers within wireless range of the user's laptop computer. A user connects the user's laptop computer to a first WiFi router. The user's laptop computer pings a first server having a static IP address and a second server having a dedicated URL (e.g., "Google.com"). Upon pinging the second server, a DNS serer in network communication with the first WiFi router resolves an IP address of the second server. A ping packet is then sent to the second server at the resolved IP address. If the user's laptop computer receives a response from the first and second servers, then the user's laptop computer maintains connectivity to first WiFi router. The user then uses the web to check his or her email or search the Internet, for example. If the user's laptop computer does not receive a response from one or both of the first and second servers, then the user's laptop computer connects to a second WiFi router.

Example 2

A user is on a plane with a plurality of network access points (WiFi hotspots). The user's Smart phone automatically scans for and generates a list of access points. Next, the user's Smart phone connects to a first network access point and pings a first server having a static IP address and a second server having a dedicated URL. Pinging the second server entails using the ping command with the URL as the destination address (e.g., "ping www.Google.com"). The DNS server will resolve the IP address of the URL to then ping the second server with the resolved IP address. If the user's Smart phone receives a response from both the first and second servers, then the user's Smart phone maintains its connection to the first network access point and the user accesses the network. If the user's Smart phone does not receive a response from one or both of the first and second servers, then the user's Smart phone connects to a second network access point and the steps above are repeated.

Example 3

A tablet PC (e.g., iPad) has a first wireless interface configured to communicate with one or more WiFi routers and a second wireless interface configured to communicate with a GSM provider. The tablet PC connects to a WiFi router using the first wireless interface and pings a first server having a static IP address and a second server having a static URL. Next, the tablet PC connects to a GSM provider using the second wireless interface and pings the first and second servers. The tablet PC then assesses, with the aid of a processor of the tablet PC, network connectivity via the WiFi router and the GSM provider to determine whether connectivity via the WiFi router and/or the GSM provider meet certain predetermined network connectivity criteria (or rules). The tablet PC determines that network connectivity via the WiFi router is preferable because it provides higher upload and download rates and is cheaper than connectivity via the GSP provider. The tablet PC then uses the WiFi router for Internet access.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of embodiments of the invention herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A network device comprising:
a plurality of network connectivity interfaces wherein at least two of said interfaces use different communication protocols;
a programmable processor programmed to perform:
a) a first network connectivity request using one of said network connectivity interfaces of the network device connected to a first access point to ping a first server and to verify end-to-end connectivity to the first server;
b) a second network connectivity request using said one of said network connectivity interfaces of the network device connected to the first access point to ping a second server and to verify end-to-end connectivity to the second server;
c) a determination whether to establish network connectivity using another of said network connectivity interfaces based on whether a response was received from said first server and whether a response was received from said second server, wherein said another of said network connectivity interfaces operates using a communication protocol different from a communication protocol of said one of said network connectivity interface and wherein said determination is also based on a network connectivity rule referencing a predetermined level of bandwidth accessible to the network-enabled device and a remaining amount of data available or consumed from its predetermined level;
d) intermittently repeating said steps a, b, c, and d to determine if failed end-to-end connectivity is caused by an error with connection pathway, the first server, or the second server, and wherein connectivity to the first server or second server is maintained if a first predetermined data packet matches a first received data packet and a second predetermined data packet matches a second received data packet.

2. The device of claim 1 wherein the programmable processor is configured to continue to sending connectivity requests until all network interfaces have been tested or at least one network pathway is confirmed for connectivity.

3. The device of claim 1 wherein the programmable processor is configured, based on connectivity pathway testing, determining if any connectivity error is caused by the servers or the connectivity pathways, and ranking connectivity pathway.

4. The device of claim 3 wherein the programmable processor is configured to maintain connectivity with a network connectivity interface with a highest ranked connectivity pathway.

5. The device of claim 1, wherein at least one of said network connectivity interface and said another network connectivity interface is a non-cellular, wireless data interface while the other is a cellular data interface.

6. The device of claim 1, wherein a data packet used for the connectivity request for said first server comprises a ping packet.

7. The device of claim 1, wherein a data packet used for the connectivity request for said second server comprises a ping packet.

8. The device of claim 1, wherein connectivity to a network provider is maintained if the first server responds to the network device in response to said pinging the first server and/or the second server responds to the network device in response to said pinging the second server.

9. The device of claim 1, further comprising connecting to another network provider if the first server does not respond to the network device in response to said pinging the first server and/or the second server does not respond to the network device in response to said pinging the second server.

10. The device of claim 1, wherein a network provider is selected from the group consisting of a wireless router, Bluetooth router, wired router, cellular network router, radiofrequency (RF) device and optoelectronic device.

11. The device of claim 1, further comprising: connecting to an additional network provider; pinging the first server with the aid of the additional network provider; pinging the second server with the aid of the additional network provider; and determining whether to maintain connectivity to the additional network provider based on whether a response was received by the network device from the first server and/or whether a response was received by the network device from the second server.

12. The device of claim 11, wherein determining whether to maintain connectivity to the additional network provider is based on whether a response was received by the network device from the first server and whether a response was received by the network device from the second server.

13. The device of claim 11, wherein connecting to said additional network provider comprises terminating connectivity to said network provider.

14. The device of claim 1, wherein a network provider is selected from the group consisting of a wireless router, Bluetooth router, wired router, cellular network router, radiofrequency (RF) device and optoelectronic device.

15. The device of claim 1, wherein the first and second servers are send connectivity requests simultaneously.

16. A network device comprising:
a plurality of network connectivity interfaces wherein at least two of said network connectivity interfaces use different communication protocols;
a programmable processor programmed to perform:
   a) a first network connectivity request using one of said network connectivity interfaces of the network device connected to a first access point to ping a first server and to verify end-to-end connectivity to the first server;
   b) a second network connectivity request using said one of said network connectivity interfaces of the network device connected to the first access point to ping a second server and to verify end-to-end connectivity to the second server;
   c) a determination whether to establish network connectivity using another of said network connectivity interfaces based upon any one network termination condition selected from the group consisting of (a) a network cost of another network provider is lower than a network cost of said network provider wherein said network connectivity interface operates differently from said another network connectivity interface; intermittently repeating said step to ping the first server and said determining step to verify network connectivity, wherein said another of said network connectivity interfaces operates using a communication protocol different from a communication protocol of said one of said network connectivity interface and wherein said determination is also based on a network connectivity rule referencing a predetermined level of bandwidth accessible to the network-enabled device and a remaining amount of data available or consumed from its predetermined level;
   d) intermittently repeating said steps a, b, c, and d to determine if failed end-to-end connectivity is caused by an error with connection pathway, the first server, or the second server, and wherein connectivity to the network provider is maintained if a first predetermined data packet matches a first received data packet and a second predetermined data packet matches a second received data packet.

17. The device of claim 16, wherein the determining step is based upon at least any two network termination conditions selected from said group.

18. The device of claim 17, wherein the determining step is based upon at least any three network termination conditions selected from said group.

19. The device of claim 16, further comprising connecting to another network provider.

20. The device of claim 16, wherein connectivity between the network device and the network provider is via a wired or wireless network access point.

* * * * *